(12) United States Patent
Bettuchi et al.

(10) Patent No.: US 7,857,789 B2
(45) Date of Patent: Dec. 28, 2010

(54) PORT FIXATION USING EXPANDABLE THREADS

(75) Inventors: Michael Bettuchi, Middletown, CT (US); Gregory Fischvogt, Hamden, CT (US); Eric Taylor, East Hampton, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/697,611

(22) Filed: Feb. 1, 2010

(65) Prior Publication Data

US 2010/0234806 A1   Sep. 16, 2010

Related U.S. Application Data

(60) Provisional application No. 61/158,818, filed on Mar. 10, 2009.

(51) Int. Cl.
   *A61M 5/178*   (2006.01)
(52) U.S. Cl. .................... 604/164.04; 604/44; 604/506; 604/158; 604/264
(58) Field of Classification Search ................ 604/506, 604/513, 158, 43–44, 93.01, 164.01, 164.04, 604/164.05, 164.06, 164.07, 164.1, 164.11, 604/164.12, 264, 272
See application file for complete search history.

(56) References Cited

U.S. PATENT DOCUMENTS

| | | | |
|---|---|---|---|
| 1,621,159 A | 3/1927 | Evans | |
| 4,043,338 A | 8/1977 | Homm et al. | |
| 4,250,873 A | 2/1981 | Bonnet | |
| 4,608,965 A | 9/1986 | Anspach, Jr. et al. | |
| 4,886,500 A * | 12/1989 | Lazarus | 604/164.01 |
| 5,209,735 A * | 5/1993 | Lazarus | 604/170.01 |
| 5,257,975 A | 11/1993 | Foshee | |
| 5,370,625 A * | 12/1994 | Shichman | 604/174 |
| 6,056,766 A * | 5/2000 | Thompson et al. | 606/185 |
| 7,070,586 B2 * | 7/2006 | Hart et al. | 604/506 |
| 2002/0193734 A1 | 12/2002 | Moenning | |
| 2007/0225650 A1 | 9/2007 | Hart et al. | |

FOREIGN PATENT DOCUMENTS

| | | |
|---|---|---|
| GB | 955490 | 10/1962 |
| WO | 2004078026 | 9/2004 |
| WO | WO 2004/078026 | 9/2004 |

OTHER PUBLICATIONS

European Search Report, Application No. 10250429 dated Jun. 10, 2010.
EP Search Report for corresponding EP10250429 mailing is Jun. 10, 2010 (3 pages).

* cited by examiner

*Primary Examiner*—Nicholas D Lucchesi
*Assistant Examiner*—Quynh-Nhu H Vu

(57) ABSTRACT

The present disclosure describes a surgical access apparatus including an access member with a longitudinal opening defining an internal dimension suitable for removable receipt of a surgical instrument. The access member has a thread mounted thereon that is movable between a first condition and a second condition. When the thread is in the first condition, the access member defines a first outer dimension that allows for positioning of the access member within a tissue tract, and when the thread is in the second condition, the access member defines a second, larger outer dimension to facilitate anchoring of the access member within the tissue tract. As the thread moves between the first and second conditions, the internal dimension of the longitudinal opening extending through the access member remains substantially constant.

19 Claims, 4 Drawing Sheets

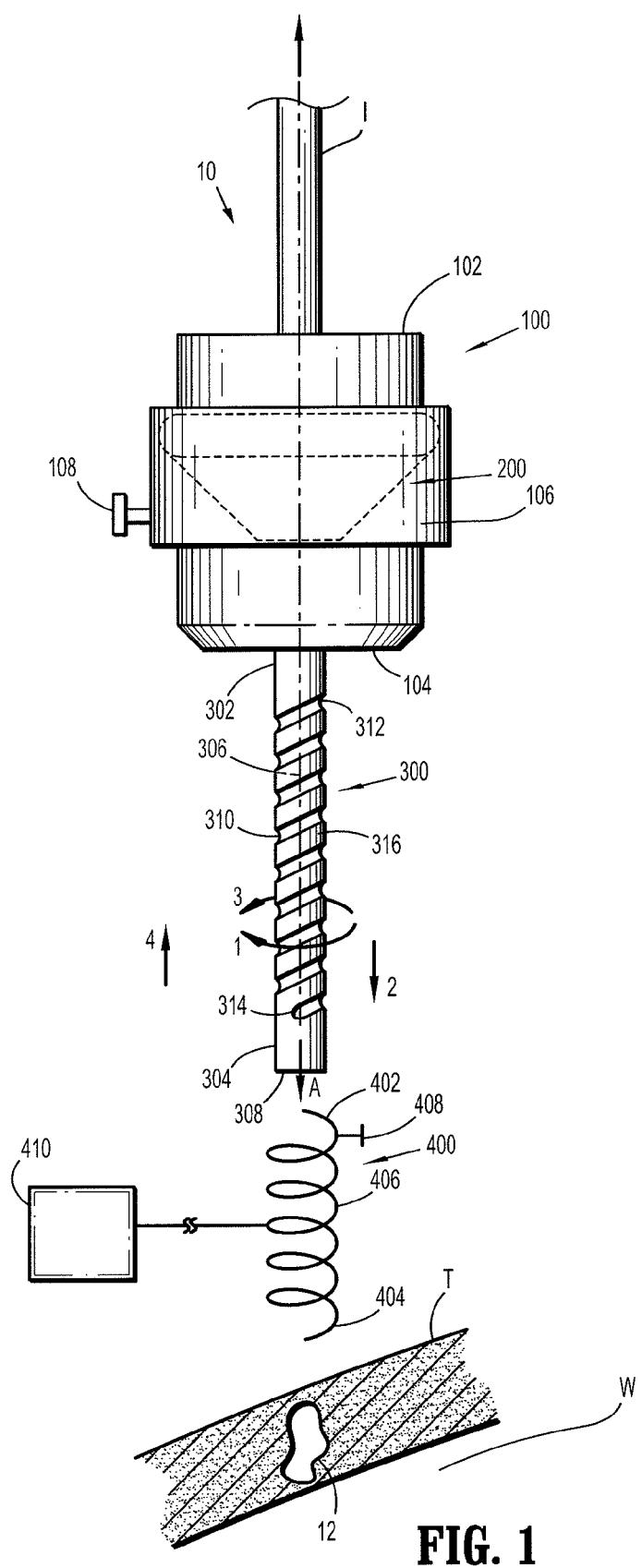
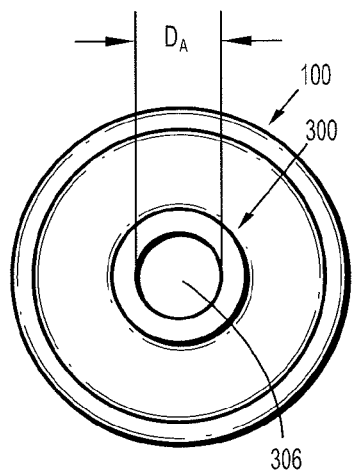
FIG. 2
FIG. 1

PORT FIXATION USING EXPANDABLE THREADS

CROSS REFERENCE TO RELATED APPLICATION

The present application claims the benefit of and priority to U.S. Provisional Application Ser. No. 61/158,818 filed on Mar. 10, 2009, the entire contents of which are incorporated herein by reference.

BACKGROUND

1. Technical Field

The present disclosure relates to surgical access apparatus for positioning within an opening formed in a patient's tissue. More particularly, the present disclosure relates to surgical access apparatus that are repositionable to facilitate anchoring within a percutaneous opening, and capable of removably receiving one or more surgical instruments.

2. Background of the Related Art

In contemporary medical practice, many surgical procedures are performed through small incisions formed in the skin, as compared to the larger incisions typically required in traditional procedures, in an effort to reduce both patient trauma and recovery time. Generally, such procedures are referred to as "endoscopic," unless performed in the patient's abdomen, in which case the procedure is referred to as "laparoscopic," or on a joint, ligament, or the like, in which case the procedure is referred to as "arthroscopic." Throughout the present disclosure, "endoscopic," "laparoscopic," and "arthroscopic" procedures may be collectively referred to as "minimally invasive" procedures.

Typically, a minimally invasive surgical procedure will include the use of a surgical access apparatus to facilitate entry into a surgical worksite positioned beneath the patient's tissue with surgical instrumentation, e.g., endoscopes, obturators, surgical staplers, and the like. A typical surgical access apparatus includes a cannula or access member defining a passageway through which the surgical instrumentation is inserted and the procedure is carried out.

While many varieties of surgical access apparatus are known in the art, a continuing need exists for a surgical access apparatus that may be releasably and reliably secured within the patient's tissue during the course of a minimally invasive procedure.

SUMMARY

In one aspect of the present disclosure, a surgical access apparatus is disclosed that is positionable within a percutaneous tissue tract to facilitate access to an underlying surgical worksite. The surgical access apparatus includes an access member with a longitudinal opening defining an internal dimension suitable for the reception of a surgical instrument. The access member has a thread mounted thereon with proximal and distal ends that is movable relative to the access member, e.g., radially and/or axially, between a first condition and a second condition.

In the first condition, the access member defines a substantially uniform outer surface, and the thread provides the access member with a first outer dimension that allows for positioning of the access member within the tissue tract. In the second condition, the access member defines a substantially non-uniform outer surface, and the thread provides the access member with a second outer dimension that is larger than the first outer dimension to facilitate anchoring of the tubular member within the tissue tract. The access member is configured and dimensioned such that the internal dimension of the longitudinal opening extending through the access member remains substantially constant as the thread moves between the first and second conditions.

The access member includes an outer surface with a helical recess having proximal and distal ends. The helical recess corresponds in configuration and dimensions to the thread such that the thread is received by the helical recess. Specifically, the thread is rotatably received by the helical recess such that the thread is rotatable for movement between the first condition and the second condition. In one embodiment, the thread may include a manual member extending outwardly therefrom that is configured and dimensioned for engagement by a clinician to facilitate rotation of the thread.

As the thread moves between the first condition and the second condition, the proximal end of the thread is displaced axially. The distal end of the thread may also be displaced axially, or alternatively, the distal end of the thread may remain in a substantially fixed axial location. In those embodiments wherein the distal end of the thread is displaced axially as the thread moves between the first condition and the second condition, it is envisioned that the distal end of the helical recess may include a ramped portion that is configured and dimensioned to engage the distal end of the thread, whereby engagement of the distal end of the thread with the ramped portion causes the distal end of the thread to move onto the outer surface of the access member. In those embodiments wherein the distal end of the thread remains in a substantially fixed axial location as the thread moves between the first condition and the second condition, it is envisioned that the distal end of the thread may be fixedly secured to the access member, e.g., formed integrally therewith. Alternatively, it is envisioned that the outer surface of the access member may include a cavity that is positioned at the distal end of the helical recess, and configured and dimensioned to receive the distal end of the thread to substantially inhibit axial movement thereof.

In an alternative embodiment of the present disclosure, the surgical access apparatus may further include a sheath that is positioned about at least a portion of the thread to inhibit contact between the thread and tissue.

The disclosed surgical access apparatus may further include a housing having a proximal end, a distal end, and a opening extending therebetween that is configured and dimensioned for removable reception of the surgical instrument, and a seal member that is positioned within the housing and adapted to removably receive the surgical instrument such that a substantially fluid-tight seal is formed therewith.

In another aspect of the present disclosure, a method of percutaneously accessing a surgical worksite positioned beneath a patient's tissue is disclosed. The method includes the steps of (i) providing a surgical access apparatus having an access member with a longitudinal opening defining an internal dimension suitable for reception of a surgical instrument, and a thread mounted thereon that is movable relative to the access member; (ii) advancing the access member distally into an opening in the tissue; and (iii) transitioning the thread of the access member from a first condition to a second condition.

In the first condition, the thread provides the access member with a first outer dimension that allows for positioning of the access member within the tissue tract, and in the second condition, the thread provides the access member with a second outer dimension that is larger than the first outer dimension to facilitate anchoring of the tubular member within the tissue tract. The access member is configured and dimensioned such that the internal dimension of the longitudinal opening extending through the access member remains substantially constant as the thread moves between the first and second conditions.

These and other features of the surgical access apparatus disclosed herein will become more readily apparent to those skilled in the art through reference to the detailed description of various embodiments of the present disclosure that follows.

BRIEF DESCRIPTION OF THE DRAWINGS

Various embodiments of the present disclosure are described herein below with references to the drawings, wherein:

FIG. 1 is a side, schematic view of a surgical access apparatus including a housing, an access member, and a fixation member in accordance with one embodiment of the present disclosure, wherein the fixation member is shown separated from the access member;

FIG. 2 is a distal end view of the housing and the access member seen in FIG. 1;

DETAILED DESCRIPTION OF THE EMBODIMENTS

Figure 3:
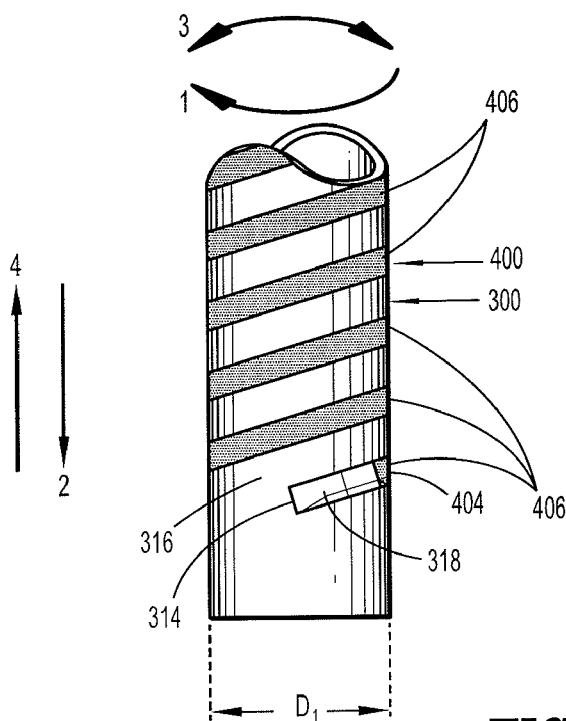
FIG. 3 is a partial side, schematic view of the access member and the fixation member seen in FIG. 1 showing the access member in a contracted condition and the fixation member in a corresponding retracted position.

In the drawings, and in the following description, like references numerals will identify similar or identical elements. Throughout the following description, the term "proximal" will refer to the end of the presently disclosed surgical access apparatus, or component thereof, that is closest to the clinician during proper use, while the "distal" will refer to the end that is furthest from the clinician. Additionally, the term "tissue tract" should be understood as referring to any opening in a patient's tissue, whether formed by the clinician or pre-existing.

FIG. 1 illustrates a surgical access apparatus 10 in accordance with the principles of the present disclosure. The surgical access apparatus 10 is removably positionable within a tissue tract or opening 12 formed in a patient's tissue "T," and is employable during the course of a surgical procedure, e.g., a minimally invasive procedure, to facilitate access to a surgical worksite "W," such as a patient's underlying cavities, tissues, organs, or the like, with one or more surgical instruments "I." The disclosed surgical access apparatus 10 includes a housing 100, a seal assembly 200, and an access member 300 including a fixation member 400.

The housing 100 may be fabricated from any suitable biocompatible material including moldable polymeric materials, stainless steel, titanium, or the like, and includes respective proximal and distal ends 102, 104. The housing 100 defines an internal cavity 106 that is configured and dimensioned to accommodate the seal assembly 200, and may be any structure suitable for this intended purpose. As depicted in FIG. 1, the housing 100 also includes a port 108 to permit the introduction of fluid, such as an insufflation gas in the case of a laparoscopic surgical procedure or an irrigant solution in the case of an arthroscopic surgical procedure, into the surgical worksite "W."

The seal assembly 200 is adapted to removably receive the surgical instrument "I" such that a substantially fluid-tight seal is formed therewith. Examples of suitable internal seals or valves are discussed in commonly assigned U.S. Pat. Nos. 5,820,600 to Carlson, et al. and 6,702,787 to Racenet et al., which issued on Oct. 13, 1998 and Mar. 9, 2004, respectively, the entire contents of which are incorporated by reference herein.

The access member 300 extends distally from the housing 100, and is dimensioned for positioning within the tissue tract 12 formed in the patient's tissue "T." The access member 300 includes respective proximal and distal ends 302, 304, and defines a longitudinal passageway 306 with an internal dimension "$D_A$" (FIG. 2). The longitudinal passageway 306 extends between the respective proximal and distal ends 302, 304 of the access member 300 along a longitudinal axis "A," and is configured and dimensioned for the internal receipt of the surgical instrument "I." The access member 300 defines an opening 308 at the distal end 304 thereof to allow the surgical instrument "I" to pass into the surgical worksite "W."

Figure 4:
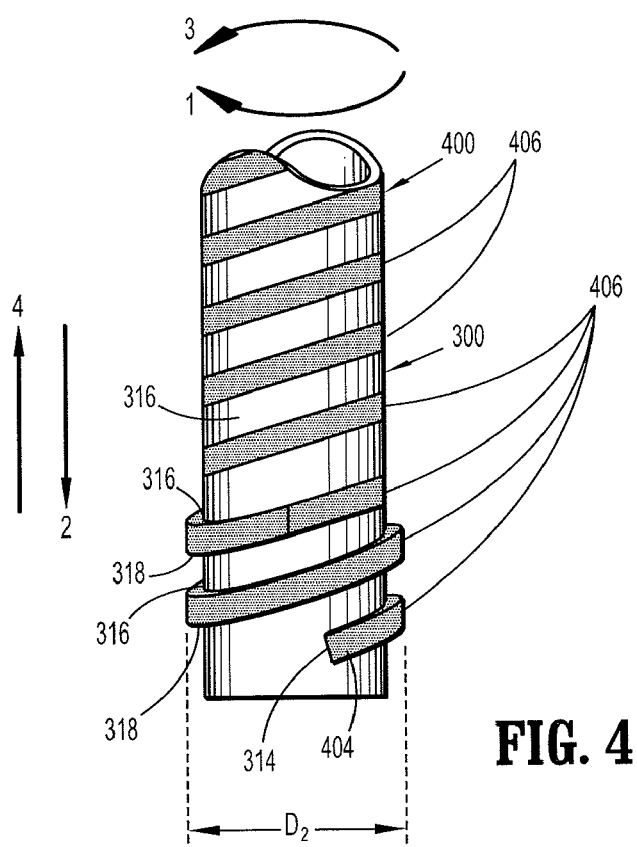
FIG. 4 is a partial side, schematic view of the access member and the fixation member illustrated in FIG. 3 showing the access member in an expanded condition and the fixation member in a corresponding advanced position.

Referring now to FIGS. 3 and 4 as well, the fixation member 400 will be discussed. The fixation member 400 may be formed from any suitable material, including but not limited to stainless steel or polymeric materials. The fixation member 400 includes proximal and distal ends 402, 404, respectively, and is configured as a coiled, helical thread 406.

The fixation member 400 is mounted coaxially about the access member 300. More specifically, the fixation member 400 is accommodated within a helical recess 310 (FIG. 1) formed in the outer surface 316 of the access member 300 and including respective proximal and distal ends 312, 314. The configuration and dimensions of the helical recess 310 correspond to those of the fixation member 400 such that when the fixation member 400 is positioned within the helical recess 310, the outer surface 316 of the access member 300 is substantially uniform or smooth, as seen in FIG. 3. Uniformity in the outer surface 316 of the access member 300 is desirable, in that such a surface minimizes the likelihood of tissue trauma upon distal advancement of the surgical apparatus 10 through the tissue tract 12 (FIG. 1).

The fixation member 400 is accommodated within the recess 310 formed in the outer surface 316 of the access member 300 such that the fixation member 400 is selectively rotatable. During rotation, the fixation member 400 is guided by the recess 310 such that the fixation member 400 moves axially along the longitudinal axis "A" between a retracted position (FIG. 3) and an advanced position (FIG. 4). For example, in the embodiment of the access member 300 discussed with respect to FIGS. 1-4, as the fixation member 400 is rotated in the direction of arrow 1, the fixation member will move axially in the direction of arrow 2 such that the respective proximal and distal ends 402, 404 of the fixation member 400 are displaced distally along the longitudinal axis "A" of the access member 300. Similarly, as the fixation member 400 is rotated in the direction of arrow 3, the fixation member will move axially in the direction of arrow 4 such that the respective proximal and distal ends 402, 404 of the fixation member 400 are displaced proximally along the longitudinal axis "A." To facilitate rotation, the fixation member may include a manual member 408 depending outwardly therefrom, as shown in FIG. 1. Alternatively, however, rotation of the fixation member 400 may be automated, e.g., driven by a motor 410 (FIG. 1).

Referring still to FIGS. 1-4, when the fixation member 400 is in the retracted position (FIG. 3), the access member 300 is in a corresponding contracted (first) condition. However, as the fixation member 400 is advanced distally in the direction of arrow 2, the distal end 404 of the fixation member 400 engages a ramped portion 318 (FIG. 3) included at the distal end 314 of the recess 310 formed in the outer surface 316 of the access member 300. When the distal end 404 of the fixation member 400 engages the ramped portion 318, the fixation member 400 begins to emerge from the recess 310 for positioning about the outer surface 316 of the access member 300 such that the access member 300 transitions into an expanded (second) condition thereof (FIG. 4).

In the contracted condition (FIG. 3), the outer surface 316 of the access member 300 is substantially uniform, as previously mentioned, and the access member 300 defines an outer dimension "$D_1$." In contrast, when the access member 300 is in the expanded condition (FIG. 4), the access member 300 includes an outer surface 316 that is non-uniform, or interrupted, due to the expansion experienced by the threads 406 of the fixation member 400. As seen in FIG. 4, the outer surface 316 of the access member 300 defines an outer dimension "$D_2$" in the expanded condition that is considerably larger than the outer dimension "$D_1$" defined by the access member 300 in the contracted condition (FIG. 3).

The smaller outer dimension "$D_1$" the access member 300 in the contracted condition (FIG. 3) reduces the axial force necessary for advancement of the surgical apparatus 10 (FIG. 1) into, and withdrawal of the surgical access apparatus 10 from, the tissue "T," thereby reducing the axial force ultimately exerted upon the tissue "T," which in turn, substantially minimizes the likelihood of trauma resulting therefrom. The larger dimension "$D_2$" defined by the access member 300 in the expanded condition (FIG. 4) anchors the access member 300 within the tissue tract 12 (FIG. 1) until such time that the access member 300 is returned to the contracted position (FIG. 3) via rotation of the fixation member 400, e.g., in the direction of arrow 3.

As the access member 300 transitions between the contracted and expanded conditions, the internal dimension "$D_A$" (FIG. 2) of the passageway 306 extending longitudinally through the access member 300 does not undergo any substantial change. Stated differently, the internal dimension "$D_A$" of the passageway 306 remains substantially constant.

During insertion of the access member 300 through the tissue tract 12 (FIG. 1), it is envisioned herein that rotation of the fixation member 400 may cause a proximal surface 412 (FIG. 4) of the threads 406 to engage the tissue "T" to facilitate further distal advancement of the access member 300. Specifically, engagement of the proximal surface 412 of the threads 406 with the tissue "T" may act to urge the access member 300 distally through the tissue tract 12 as the fixation member 400 is rotated, e.g., in the direction of arrow 1, thus allowing the access member 300 to be effectively screwed into the tissue "T." Similarly, during withdrawal of the access member 300 from the tissue tract 12 (FIG. 1), it is envisioned that rotation of the fixation member 400 may cause a distal surface 414 (FIG. 4) of the threads 406 to engage the tissue "T" to facilitate proximal advancement of the access member 300. Specifically, engagement of the distal surface 414 of the threads 406 with the tissue "T" may act to urge the access member 300 proximally from the tissue tract 12 (FIG. 1) as the fixation member 400 is rotated, e.g., in the direction of arrow 3, thus allowing the access member 300 to be effectively screwed out of the tissue "T." This screw-like motion will substantially limit the axial force exerted upon the tissue "T" during insertion and removal of the access member 300, thus substantially minimizing the likelihood of any trauma resulting therefrom.

With continued reference to FIGS. 1-4, the use and function of the surgical access apparatus 10 (FIG. 1) will be discussed during the course of a typical minimally invasive surgical procedure subsequent to formation of the tissue tract 12.

Prior to insertion of the surgical access apparatus 10, to facilitate placement and positioning of the access member 300 within the tissue tract 12, the clinician ensures that the fixation member 400 is in the retracted position (FIG. 3), and consequently, that the access member 300 is in the contracted position. The clinician then positions the distal end 304 (FIG. 1) of the access member 300 within the tissue tract 12 and advances the surgical access apparatus 10 towards the tissue "T" until the distal end 404 of the fixation member 400 is positioned beneath the tissue "T." Thereafter, the clinician effectuates rotation of the fixation member 400, e.g., via the manual member 408 (FIG. 1), to move the fixation member from the retracted position (FIG. 3) into the advanced position (FIG. 4), and thereby transition the access member 300 into the expanded condition.

As the fixation member 400 rotates, e.g., in the direction of arrow 1, the fixation member 400 moves distally along the longitudinal axis "A" of the access member 300 in the direction of arrow 2 until the distal end 404 of the fixation member 400 engages the ramped portion 318 (FIG. 3). Engagement with the ramped portion 318 causes the distal end 404 of the fixation member to ride up onto the outer surface 316 of the access member 300, thereby transitioning the access member 300 transitions into the expanded (second) condition (FIG. 4), and anchoring the surgical access apparatus 10 within the tissue tract 12 (FIG. 1). The surgical instrument "I" can then be inserted into, and advanced distally through, the passageway 306 (FIGS. 1, 2) extending through the access member 300 to carry out the surgical procedure through the surgical access apparatus 10.

After completing the procedure and withdrawing the surgical instrument "I" from the access member 300, the clinician rotates the fixation member 400, e.g., in the direction of arrow 3, such that the fixation member 400 moves proximally along the longitudinal axis "A" of the access member 300 in the direction of arrow 4. Continued rotation will cause the fixation member 400 to recede into the recess 310 (FIG. 1) formed in the outer surface 316 of the access member 300, thereby returning the fixation member 400 to the retracted position (FIG. 3) and the access member 300 to the contracted position. The surgical access apparatus 10 can then be withdrawn from the tissue tract 12 (FIG. 1), and the tissue tract 12 can be closed.

Figure 5:
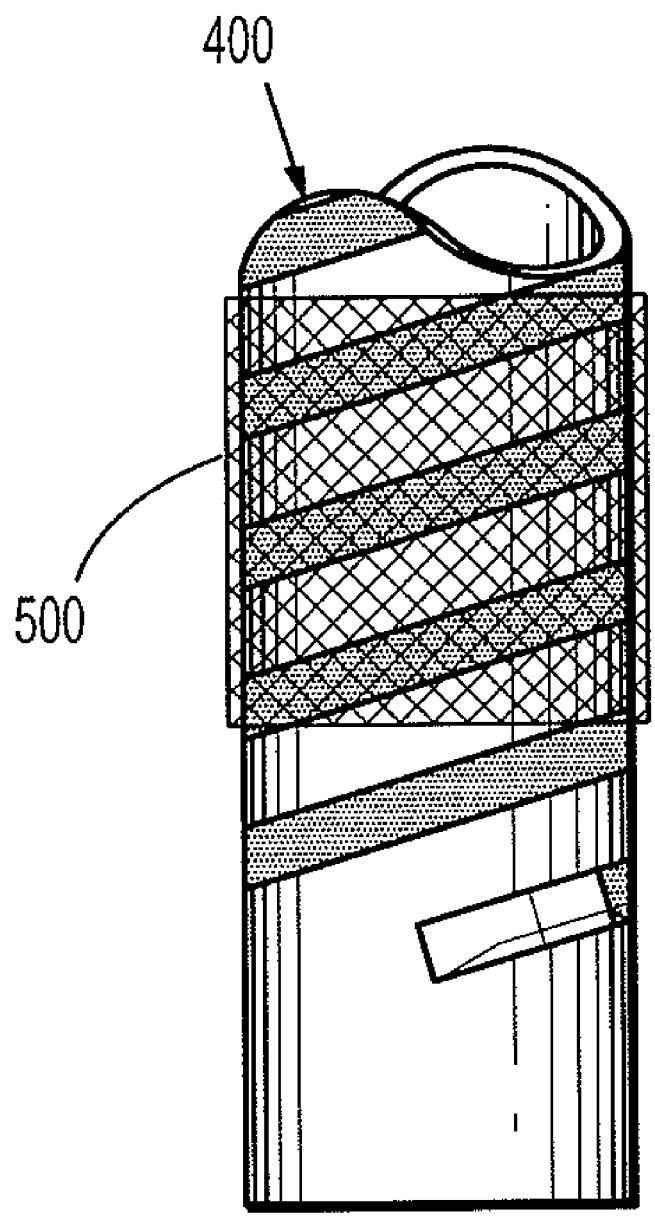
FIG. 5 is a partial side, schematic view of an alternative embodiment of the present disclosure including a sheath positioned about at least a portion of the fixation member.

Referring now to FIG. 5, the surgical access apparatus 10 (FIG. 1) may further include a sheath or guard 500 that is positioned about the fixation member 400 to inhibit contact between the fixation member 400 and the tissue "T" (FIG. 1). The sheath 500 may be positioned about the entirety of the fixation member 400, or alternatively, about only a portion of the fixation member 400, as shown in FIG. 5. The sheath 500 may be formed from any suitable biocompatible material, including but not limited to polymeric materials or rubber.

Figure 6:
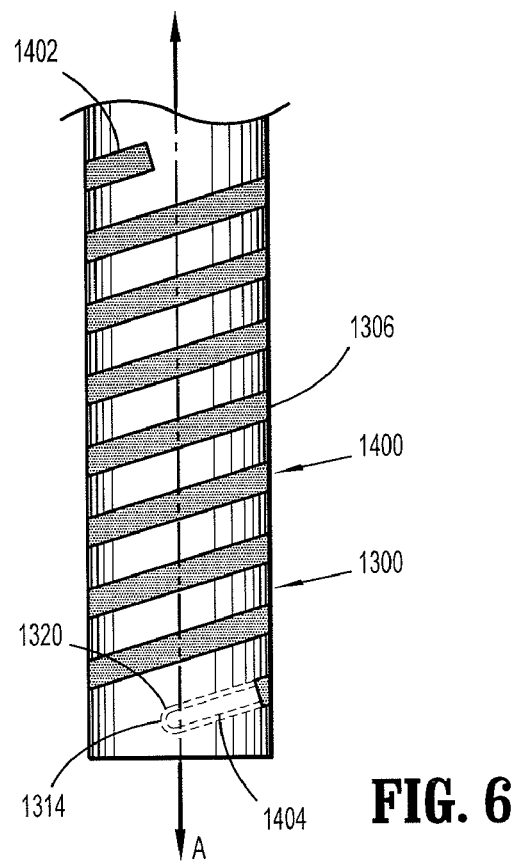
FIG. 6 is a partial side, schematic view illustrating an alternative embodiment of the access member seen in FIG. 1 showing the access member in a contracted condition and the fixation member in a corresponding retracted position.
Figure 7:
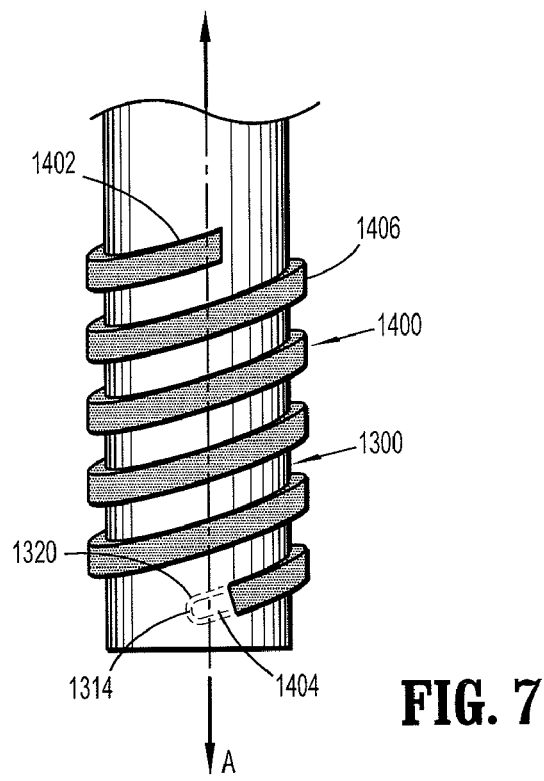
FIG. 7 is a partial side, schematic view of the access member and the fixation member illustrated in FIG. 6 showing the access member in an expanded condition and the fixation member in a corresponding advanced position.

FIGS. 6 and 7 illustrate an alternate embodiment of the presently disclosed access member, which is identified by the reference characters 1300, in conjunction with the fixation member 400 discussed above with respect to FIGS. 1-4. The access member 1300 is substantially similar to the aforedescribed access member 300, and accordingly, will only be discussed with respect to its differences therefrom.

The access member 1300 is adapted to permit relative movement between the proximal end 402 of the fixation member 400 and the access member 1300 during rotation of the fixation member 400, while substantially preventing relative movement between the distal end 404 of the fixation member 400 and the access member 1300. As a result, rotation of the fixation member 400, i.e., to cause movement from the retracted position (FIG. 6) to the advanced position (FIG. 7), results in approximation of the respective proximal and distal ends 402, 404 of the fixation member 400. This approximation in turn causes outward expansion of the fixation member 400, i.e., away from the longitudinal axis "A," such that access member 1300 realizes the expanded condition illustrated in FIG. 7.

In one embodiment, as seen in FIGS. 6 and 7, it is envisioned that the distal end 404 of the fixation member 400 may be received by a pocket or cavity 1320 formed in the access member 1300. As the fixation member 400 rotates, e.g., in the direction of arrow 1 (FIG. 6), the distal end 404 thereof engages the internal surfaces of the cavity 1320, thereby inhibiting movement of the distal end 404 of the fixation member 400 relative to the and the access member 1300. Alternatively, it is envisioned that the distal end 404 of the fixation member 400 may be secured to, e.g., integrally formed with, the access member 1300 to prevent relative movement therebetween.

To maintain the expanded condition of the access member 1300 (FIG. 7), and thus, anchoring of the surgical access apparatus 10 (FIG. 1) within the tissue "T," the surgical access apparatus 10 may include any suitable mechanism. For example, the surgical access apparatus 10 may incorporate ratcheting structure (not shown) associated with either or both of the access member 1300 and the fixation member 400. Alternatively, the surgical access apparatus may include a lockable collar, or other such structure, that is engagable with the fixation member 400 and repositionable along the longitudinal axis "A" of the access member 1300.

The above description, disclosure, and figures should not be construed as limiting, but merely as exemplary of particular embodiments. It is to be understood, therefore, that the disclosure is not limited to the precise embodiments described, and that various other changes and modifications may be effected by one skilled in the art without departing from the scope or spirit of the disclosure. Additionally, those skilled in the art will appreciate that the elements and features illustrated or described in connection with one embodiment can be combined with those of another, and that such modifications and variations are also intended to be included within the scope of the present disclosure.

What is claimed is:

1. A surgical access apparatus which comprises:
   an access member dimensioned for insertion and passage through tissue to permit access to an underlying surgical site, the access member defining a longitudinal axis and having a longitudinal opening for reception of a surgical instrument; and
   a non-inflatable thread mounted about the access member and being movable relative to the access member between a first condition, in which the thread provides the access member with a first outer dimension to allow for positioning of the access member within the tissue tract, and a second condition, in which the thread provides the access member with a second outer dimension larger than the first outer dimension to facilitate anchoring of the tubular member within the tissue, the thread operatively coupled to the access member in a manner whereby, subsequent to performing a surgical task, the access member and the thread are removable from the tissue.

2. The surgical access apparatus of claim 1, wherein the thread is radially moveable relative to the access member.

3. The surgical access apparatus of claim 1, wherein the thread is axially moveable relative to the access member.

4. The surgical access apparatus of claim 1, wherein the access member is configured and dimensioned such that the internal dimension of the longitudinal opening extending through the access member remains substantially constant as the thread moves between the first and second conditions.

5. The surgical access apparatus of claim 1, wherein the access member defines a substantially uniform outer surface when the thread is in the first condition and a non-uniform outer surface when the thread is in the second condition.

6. The surgical access apparatus of claim 1, wherein the access member includes an outer surface with a helical recess having proximal and distal ends and corresponding in configuration and dimensions to the thread such that the thread is received by the helical recess.

7. The surgical access apparatus of claim 6, wherein the thread is rotatably received by the helical recess such that the thread is rotatable for movement between the first condition and the second condition.

8. The surgical access apparatus of claim 7, wherein the thread includes a manual member configured and dimensioned for engagement by a clinician to facilitate rotation of the thread.

9. The surgical access apparatus of claim 8, wherein the manual member is dimensioned to extend outwardly from the thread.

10. The surgical access apparatus of claim 6, wherein the proximal end of the thread is displaced axially as the thread moves between the first condition and the second condition.

11. The surgical access apparatus of claim 10, wherein the distal end of the thread is displaced axially as the thread moves between the first condition and the second condition.

12. The surgical access apparatus of claim 11, wherein the distal end of the helical recess includes a ramped portion configured and dimensioned to engage the distal end of the thread as the thread moves in a distal direction during movement from the first condition to the second condition, whereby engagement of the distal end of the thread and the ramped portion causes the distal end of the thread to move onto the outer surface of the access member.

13. The surgical access apparatus of claim 10, wherein the distal end of the thread remains in a substantially fixed axial location as the thread moves between the first condition and the second condition.

14. The surgical access apparatus of claim 13, wherein the distal end of the thread is fixedly secured to the access member.

15. The surgical access apparatus of claim 13, wherein the distal end of the thread is formed integrally with the access member.

16. The surgical access apparatus of claim 13, wherein the outer surface of the access member includes a cavity positioned at the distal end of the helical recess, the cavity being configured and dimensioned to receive the distal end of the thread to substantially inhibit axial movement thereof.

17. The surgical access apparatus of claim 1, wherein the surgical access apparatus further includes a housing having a proximal end, a distal end, and a opening extending therebetween configured and dimensioned for removable reception of the surgical instrument, and a seal member positioned within the housing, the seal member being adapted to removably receive the surgical instrument such that a substantially fluid-tight seal is formed therewith.

18. The surgical access apparatus of claim 1, wherein the surgical access apparatus further includes a sheath positioned about at least a portion of the thread to inhibit contact between the thread and tissue.

19. A method of percutaneously accessing a surgical worksite positioned beneath a patient's tissue, the method comprising the steps of:

provinding a surgical access apparatus comprising:

an access member including a longitudinal opening defining an internal dimension suitable for reception of a surgical instrument, the access member having mounted thereon a non-inflatable thread being movable relative to the access member;

advancing the access member distally into an opening in the tissue; and transitioning the thread of the access member from a first condition, in which the thread provides the access member with a first outer dimension to allow for positioning of the access member within the tissue tract, to a second condition, in which the thread provides the access member with a second outer dimension larger than the first outer dimension to facilitate anchoring of the tubular member within the tissue tract, wherein the access member is configured and dimensioned such that the internal dimension of the longitudinal opening extending through the access member remains substantially constant as the thread moves between the first and second conditions, removing the access member with the thread from the tissue.

* * * * *